United States Patent [19]

Sakurai et al.

[11] Patent Number: 4,542,099

[45] Date of Patent: Sep. 17, 1985

[54] METHOD FOR MANUFACTURING RESTRICTION ENZYMES FROM BIFIDOBACTERIA

[75] Inventors: Toshizo Sakurai; Toshiyuki Kosaka, both of Tokyo, Japan

[73] Assignee: Kabushiki Kaisha Yakult Honsha, Tokyo, Japan

[21] Appl. No.: 240,363

[22] Filed: Mar. 4, 1981

[30] Foreign Application Priority Data

Apr. 2, 1980 [JP] Japan .................................. 55-43857

[51] Int. Cl.$^4$ ............................ C12N 9/22; C12R 1/01
[52] U.S. Cl. ...................................... 435/199; 435/822
[58] Field of Search ........................................ 435/199

[56] References Cited

U.S. PATENT DOCUMENTS 4,064,011 12/1977 Mayer et al. .......................... 435/199
4,161,424 7/1979 Ando et al. ........................... 435/199
4,259,446 3/1981 Ando et al. ........................... 435/199

OTHER PUBLICATIONS

Roberts in Methods in Enzymology, vol. 68, pp. 27 to 41 (1979).

Primary Examiner—Lionel M. Shapiro
Attorney, Agent, or Firm—Wenderoth, Lind & Ponack

[57] ABSTRACT

This invention relates to a method for manufacturing restriction enzymes, which comprises cultivating a restriction enzyme-producing strain belonging to Bifidobacterium and recovering the restriction enzyme from the bacteria thus cultivated.

2 Claims, No Drawings

METHOD FOR MANUFACTURING RESTRICTION ENZYMES FROM BIFIDOBACTERIA

BACKGROUND OF THE INVENTION

This invention relates to restriction enzymes from Bifidobacteria and the method for manufacturing the enzymes.

Restriction enzymes are endonucleases which recognize specific nucleotide sequences on double-stranded deoxyribonucleic acid (DNA) and cleave it at or near the sequences, yielding unique fragments of DNA.

Since the discovery of a restriction enzyme in *Haemophilus influenzae*, a number of restriction enzymes have been isolated from a broad range of bacteria (Roberts, 1980).

Due to their unique property of dissecting DNA at specific sites, these enzymes have found usefullness in a wide variety of applications in DNA research, including physical mapping of genes, DNA sequence analyses, gene isolation, and recombinant DNA technique.

While many restriction enzymes of different specificity are known, it is still required to have novel specificities for further characterization of DNA molecules and for the construction of recombinant DNA molecules in vitro, and to have better sources of some of the known enzymes for practical purposes.

We have examined many species of nonpathogenic, intestinal bacteria for the presence of restriction enzymes, and found that Bifidobacteria produce a variety of these enzymes with properties advantageous to practical use.

Bifidobacteria are easy to grow on a large scale, and the enzymes can be purified in a straightforward manner because of their remarkable stability and the low level of interfering nuclease activities in the crude extracts.

Among Bifidobacteria screened for restriction enzymes, 8 in 15 strains from 9 species showed enzyme activities. These strains are listed below.

B. *bifidum* YIT4007: FERM-P 5871
B. *breve* YIT4006: FERM-P 3906
B. *infantis* 659: ATCC25962
B. *infantis* S76e: ATCC15702
B. *longum* E194b: ATCC15707
B. *thermophilum* RU 326: ATCC25866
B. *breve* S1: ATCC15700
B. *breve* S50: ATCC15698

SUMMARY OF THE INVENTION

This invention is concerning the method for manufacturing restriction enzymes of differing specificity from nonpathogenic, intestinal bacteria, Bifidobacteria. These enzymes have been detected in 8 strains from 5 species, and some of them have been partially purified and characterized.

DESCRIPTION OF THE PREFERRED EMBODIMENT

The cultivation of a restriction enzyme-producing strain of the present invention can be carried out in any conventional manner in any conventional medium. Therefore, the process of cultivation and the medium used therein should not be specially limited.

For the preparation of restriction enzymes from Bifidobacteria, cells were grown at 37° C. in an appropriate, anaerobic medium to early stationary phase. This means that the culture does not have to be monitored carefully. The cells were harvested by centrifugation, and stored at −2020 C. until use.

A typical method of purifying restriction enzymes from Bifidobacteria is described below. Frozen cell pellets were thawed and suspended in 4 vol of 10 mM $K_2HPO_4$-$KH_2PO_4$, pH 7.0, 7 mM 2-mercaptoethanol, 1 mM EDTA (buffer A) containing 25 μg phenylmethyl sulfonylfluoride (PMSF), 1 mM $NaN_3$ and 0.4M NaCl.

The cell suspension was treated on ice with lysozyme (100 μg/ml) to make the cells susceptible to sonication. Sonication was carried out until more than 90% of the cells were disrupted. Care was taken to keep the temperature below 10° C. All subsequent operations were carried out below 5° C.

The sonicated cell suspension was centrifuged at $100,000 \times g$ for 1 h and the supernatant was decanted. A 10% (w/v) solution of streptomycin sulfate was slowly added to a final concentration of 1.2%. After stirring for at least 30 min, the precipitated nucleic acids were removed by low speed centrifugation.

The DNA-free supernatant was fractionated with ammonium sulfate, and the fraction containing restriction enzyme activity was further purified by combinations of gel filtration, ion-exchange and affinity chromatographies. Usually two or three steps of column chromatography were sufficient to obtain partially purified enzyme essentially free of contaminating nucleases.

Restriction enzymes purified from Bifidobacteria share some properties in common. One of the advantageous properties is their remarkable stability, and thus these enzymes can be purified without substantial loss of activity in the absence of glycerol or serum albumin.

As described above, 8 in 15 strains from 9 species so far examined showed restriction enzyme activities, and these enzymes were named according to the nomenclature of Smith and Nathans (1973) (Table 1). We have not yet purified and characterized all the enzymes listed in Table 1, but some general properties have been observed for partially purified enzymes.

(1) Substrate specificity

Restriction enzymes from 8 strains of Bifidobacteria were examined for their substrate specificity with standard DNAs. The DNAs used were *E. coli* phage λ DNA, *E. coli* phage φX174 RFI DNA, animal virus adenovirus type 2 DNA, and animal virus SV40 DNA. The enzyme digests of these DNAs were analyzed by electrophoresis on agarose gel, and the digest patterns were photographed under UV light. As shown in Table 2, most of these enzymes seem to be different in their substrate specificity.

(2) pH optimum

The pH optimum of these enzymes is between pH 6.8 and 8.0.

(3) Optimal temperature

The optimal temperature of these enzymes is around 37° C.

(4) Inhibition, activation and stabilization

The presence of $Mg^{2+}$ is essential, but neigther adenosine triphosphate nor S-sdenoxylmethyonine is required. Monovalent cations are not required and inhibit the enzyme activity at higher concentrations.

TABLE 1

| Restriction enzymes in Bifidobacteria | | |
|---|---|---|
| Strain | Source | Enzyme |
| B. bifidum | YIT 4007 | Bbi I |
| | | Bbi II |
| B. breve S1 | ATCC 15700 | Bbe SI |
| B. breve S50 | ATCC 15698 | Bbe AI |
| B. breve | YIT 4006 | Bbe I |
| | | Bbe II |
| B. infantis 659 | ATCC 25962 | Bin I |
| B. infantis S76e | ATCC 15702 | Bin SI |
| B. longum E194b | ATCC 15707 | Blo I |
| B. thermophilum | ATCC 25866 | Bth I |

TABLE 2

| | | | | Number of cleavage sites | | | |
|---|---|---|---|---|---|---|---|
| Strain | Source | Enzyme | Sequence | Lambda | Ad2 | SV40 | ØX174 |
| B. bifidum | YIT 4007 | Bbi I | CTGCAG | 18 | 25 | 2 | 1 |
| | | Bbi II | GRCGYC | ≧14 | ≧14 | 0 | 7 |
| B. breve S1 | ATCC 15700 | Bbe SI | | + | + | | |
| B. breve S50 | ATCC 15698 | Bbe AI | | + | + | | |
| B. breve | YIT 4006 | Bbe I | GGCGCC | 1 | ≧18 | 0 | 2 |
| B. infantis 659 | ATCC 25962 | Bin I | | + | + | 5 | 0 |
| B. infantis S76e | ATCC 15702 | Bin SI | | + | + | + | 0 |
| B. longum E194b | ATCC 15707 | Blo I | | + | + | | |
| B. thermophilum | ATCC 25866 | Bth I | CTCGAG | 1 | 6 | 0 | 1 |

The present invention is further illustrated by the following Examples, but is not limited thereto.

EXAMPLE 1

A strain of *Bifidobacterium thermophilum* (ATCC 25866) was grown on modified VL-G medium (Azuma and Suto, 1970) prepared according to the modified Hungate method (Azuma and Suto, 1970; Hungate, 1969). The modified VL-G medium contains in 1 liter: 75 ml of 0.1% $K_2HPO_4$ (salt solution I), 75 ml of salt solution II consisting of 0.6% $KH_2PO_4$, 1.2% $(NH_4)_2SO_4$, 1.2% NaCl, 0.12% $MgSO_4.7H_2O$, and 0.12% $CaCl_2.2H_2O$, 0.1% resazulin 0.1 ml, Trypticase 1 g, yeast extract 0.5 g, meat extract 0.2 g, glucose 0.5 g, 8% $Na_2CO_3$ 5 ml, 3% cysteine-HCl 1 ml, and distilled water 790 ml.

For the preparation on a small scale, modified VL-G medium (6×1 liter) was inoculated with its 250th volume of overnight culture of *B. thermophilum*, and the cells were grown at 37° C. for about 15 h to early stationary phase, harvested by centrifugation and stored at −20° C. The yield was about 25 g.

The DNA-free cell extract was prepared as described in DESCRIPTION OF THE PREFERRED EMBODIMENT. Solid ammonium sulfate was added to the DNA-free extract over a period of 30 min to yield 55% saturation. After stirring for 1 h at 0° C., the precipitate was collected by centrifugation at 12,000 rpm for 25 min, suspended in a minimum volume of buffer A, and dialyzed against three changes of the buffer.

The dialysate was loaded onto a Whatman P-11 phosphocellulose column (1.5×25 cm), previously equilibrated with buffer A. After washing with 90 ml of the buffer, the column was developed with a 300 ml linear gradient of 0–0.5M NaCl in buffer A. Enzyme activity eluted at 0.05–0.15M NaCl.

The active fractions were pooled and dialyzed against three changes of 10 mM Tris-HCl, pH 7.4, 7 mM 2-mercaptoethanol, 1 mM EDTA (buffer B). The pool was applied to a Whatman DEAE-cellulose DE52 column (1.0×20 cm), previously equilibrated with buffer B. After washing with 30 ml of the buffer, the column was eluted with 150 ml linear gradient of 0–0.5M NaCl. Those fractions containing enzyme activity eluting at 0.25–0.35M NaCl were combined, dialyzed against buffer B containing 0.25M NaCl, and loaded onto a heparin-Sepharose CL-6B column (1.0×7 cm), previously equilibrated with the same buffer. After washing, the column was developed with a 60 ml linear gradient of NaCl in buffer B. Enzyme activity eluted at 0.4–0.5M NaCl. The active fractions were pooled, concentrated by dialysis against buffer B containing 50% glycerol, and stored at −20° C.

After incubation with excess enzyme for a prolonged period, the BthI digest of λ DNA gave sharp bands, with no smearing, on agarose gel. As presented in Table 2, SV40 DNA is not cleaved by BthI. When superhelical SV40 DNA was incubated with excess enzyme for an extended period, no significant conversion of this DNA to the nicked circular form was seen. These results indicate no detectable contamination of the partially purified BthI with nonspecific nucleases.

Comparison of the cleavage products obtained with several DNA molecules showed BthI to be an isoschizomer of XhoI, which is known to recognize the nucleotide sequence 5'-CTCGAG-3'.

EXAMPLE 2

*B. breve* YIT4006 was grown as described for *B. thermophilum*. The yield was about 35 g from 6 liter culture.

The DNA-free extract was prepared as for BthI, and fractionated with ammonium sulfate. Most enzyme activity was found in 40–60% cut and suspended in buffer A containing 0.1M NaCl. After dialysis against the same buffer, the dialysate was applied onto a Whatman phosphocellulose P-11 column (1.5×35 cm), previously equilibrated with buffer A containing 0.1M NaCl. The column was rinsed and developed with a 450 ml linear gradient of 0.1–0.6M NaCl in buffer A. Enzyme activity eluting at 0.25–0.35M NaCl was pooled and dialyzed against buffer B.

A Whatman DEAE-cellulose DE52 column (1.0×15 cm) was prepared and equilibrated with buffer B. The phosphocellulose fractions were loaded onto the column. After washing, the column was eluted with a 120 ml gradient of 0–0.5M NaCl in buffer B.

The active fractions eluting at 0.20–0.25M NaCl were combined, dialyzed against buffer B containing 0.25M NaCl, applied onto a heparin-Sepharose CL-68 column (1.0×5 cm), previously equilibrated with the same buffer. After washing, the column was developed with a 40 ml gradient of 0.25–0.75 NaCl. Enzyme activity was recovered in fractions at 0.4–0.5M NaCl. These fractions were pooled, concentrated by dialysis against buffer B containing 50% glycerol, and stored at −20° C.

Partially purified enzyme, BbeI, was found to be essentially free of contaminating nonspecific nucleases, because after prolonged incubation with excess enzyme, BbeI digest of λ DNA yielded the fragment pattern showing no band widening on agarose gel, and only a trace amount of non-substrate SV40 DNA was converted from the superhelical to the relaxed form.

BbeI cleaves several standard DNAs as shown in Table 2. Based on these cleavage patterns, it can be deduced that the recognition sequence for BbeI is probably a palindromic hexanucleotide GGCGCC. Since this enzyme shows a new sequence specificity, it should be especially valuable in DNA research.

EXAMPLE 3

B. bifidum YIT4007 was grown in modified VL-G medium as described for B. thermophilum. The yield was about 25 g from 6 liter culture.

The DNA-free extract was prepared as described above, and solid ammonium sulfate was added to achieve 65% saturation. The precipitate was collected by centrifugation, dissolved in 10 mM $K_2HPO_4$-$KH_2PO_4$, pH 7.4, 7 mM 2-mercaptoethanol, 1 mM EDTA (buffer C), and dialyzed against the buffer.

A Whatman phosphocellulose P-11 column (1.5×35 cm) was prepared and equilibrated with buffer C, and the dialysate was applied onto the column. After washing, the column was eluted with a 450 ml gradient of 0–0.7M NaCl in buffer C. At least two different enzyme activities have been resolved, and named BbiI and BbiII, respectively. BbiI flowed through the column, while BbiII eluted at 0.1–0.2M NaCl.

Flowthrough and washes containing BbiI activity were pooled, precipitated by adding ammonium sulfate to yield 60% saturation, and suspended in a minimum volume of buffer B containing 0.1M NaCl. It was loaded onto a Sephadex G-200 column (2.5×55 cm), previously equilibrated with the above buffer, and the column was run with buffer B containing 0.1M NaCl. BbiI activity eluted at 0.6–0.8 bed volume, was pooled, and dialyzed exhaustively against buffer B.

A Whatman DEAE-cellulose DE-52 column (1.0×10 cm) was prepared and equilibrated with buffer B. BbiI Sephadex fraction was applied onto the column. After washing, the column was developed with a 80 ml gradient of 0–0.5M NaCl in buffer B. Enzyme activity eluted at 0.25–0.30M NaCl, was combined, and dialyzed against buffer A containing 0.2M NaCl.

The dialysate was loaded onto a hydroxylapatite column (1.0×10 cm), previously equilibrated with buffer A containing 0.2M NaCl. The column was washed and eluted with a 80 ml gradient of 0.01–0.5M potassium phosphate in buffer A containing 0.2M NaCl. BbiI eluted at 0.1–0.25M potassium phophate.

The specificity of BbiI was examined with several standard DNAs and compared with the digest patterns of known enzymes. The similarity of BbiI and PstI digest patterns was observed. The fragment patterns obtained from λ DNA or adenovirus type 2 DNA digested with PstI alone were identical to those obtained from the same DNAs digested with BbiI followed by PstI. This indicates that BbiI is an isoschizomer of PstI, recognizing a symmetrical hexanucletide CTGCAG.

BbiI is much more stable than PstI, and is advantageous for practical use.

BbiII active fractions were combined and dialyzed against buffer A containing 0.2M NaCl. It was loaded onto a hydroxyl-apatite column (1.0×10 cm), previously equilibrated with the above buffer. After washing, the column was developed with 80 ml gradient of 0.01–0.5M potassium phosphate in buffer A containing 0.2M NaCl. Enzyme activity eluted at 0.05–0.1M potassium phosphate.

Preliminary experiments showed that BbiII is an isoschizomer of AcyI, which recognize a related hexanucleotide GRCGYC where R is purine base and Y is pyrimidine base. AcyI is isolated from *Anabaena cylindrica*, a strain of blue-green algae. The culture of this microorganism is laborious and time-consuming. Thus, *B. bifidum* YIT4007 is much better source for this enzyme than *A. cylindrica*.

What we claim is:

1. A method for manufacturing restriction enzymes, which comprises cultivating a restriction enzyme-producing strain belonging to Bifidobacterium and recovering the restriction enzyme from the bacteria thus cultivated.

2. A method according to claim 1 wherein the restriction enzyme-producing strain is a member selected from the group consisting of *B. bifidum* YIT 4007 (FERM-P5871), *B. breve* YIT 4006 (FERM-P 3906), *B. infantis* 659 (ATCC 25962), *B. infantis* S76e (ATCC 15702), *B. longum* E194b (ATCC 15707), *B. thermophilum* RU 326 (ATCC 25866), *B. breve* S1 (ATCC 15700) and *B. breve* S50 (ATCC 15698).

* * * * *